United States Patent [19]

Anno

[11] 4,031,008
[45] June 21, 1977

[54] ARTIFICIAL KIDNEY DEVICE

[75] Inventor: Gousuke Anno, Kawasaki, Japan

[73] Assignee: Tokyo Shibaura Electric Co., Ltd., Tokyo, Japan

[22] Filed: Dec. 22, 1975

[21] Appl. No.: 643,301

Related U.S. Application Data

[63] Continuation-in-part of Ser. No. 529,500, Dec. 4, 1974, Pat. No. 3,986,956.

[30] Foreign Application Priority Data

Dec. 23, 1974 Japan .............................. 49-147859

[52] U.S. Cl. ............................ 210/137; 210/321 B
[51] Int. Cl.² ........................................ B01D 31/00
[58] Field of Search ................. 128/DIG. 13, 214 F; 210/22, 321 B, 321 R

[56] References Cited

UNITED STATES PATENTS 3,228,397   1/1966   Moss .......................... 128/DIG. 13
3,365,061   1/1968   Bray .......................... 210/321 R X Primary Examiner—Frank A. Spear, Jr.
Attorney, Agent, or Firm—Finnegan, Henderson, Farabow & Garrett

[57] ABSTRACT

In an artificial kidney device comprising a dialyzer for removing specified components from blood wherein an ultrafiltration pressure is applied to the dialyzer, an ultrafiltration pressure adjusting means is provided midway of a tube for transporting the blood passed through the dialyzer into a vein of a human being, which comprises a double walled tube consisting of an easily deformable inner tube communicating with the blood transporting tube and a rigid outer tube surrounding the inner tube to define a closed chamber therebetween, pressure applying means for applying pressure to the interior of the closed chamber and an air reservoir communicating with the closed chamber and provided with a partition means near an outlet to the closed chamber for harmetically dividing the air reservoir into two rooms.

34 Claims, 11 Drawing Figures

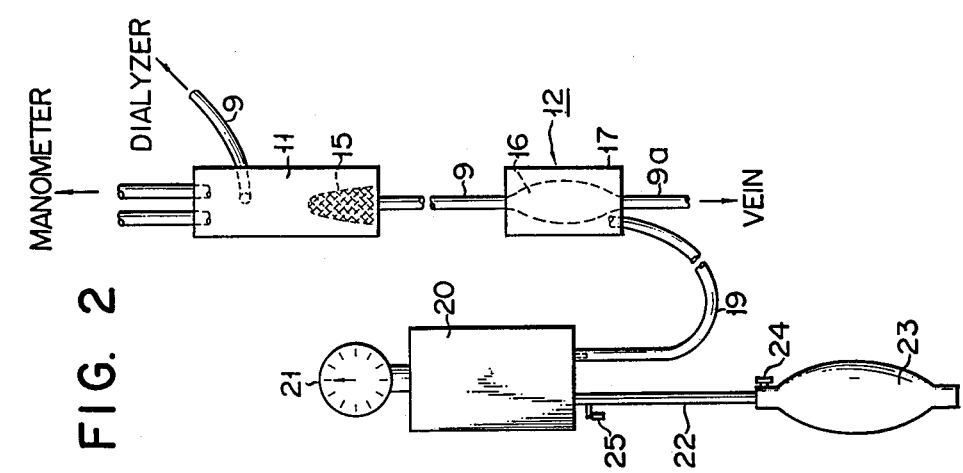
FIG. 2
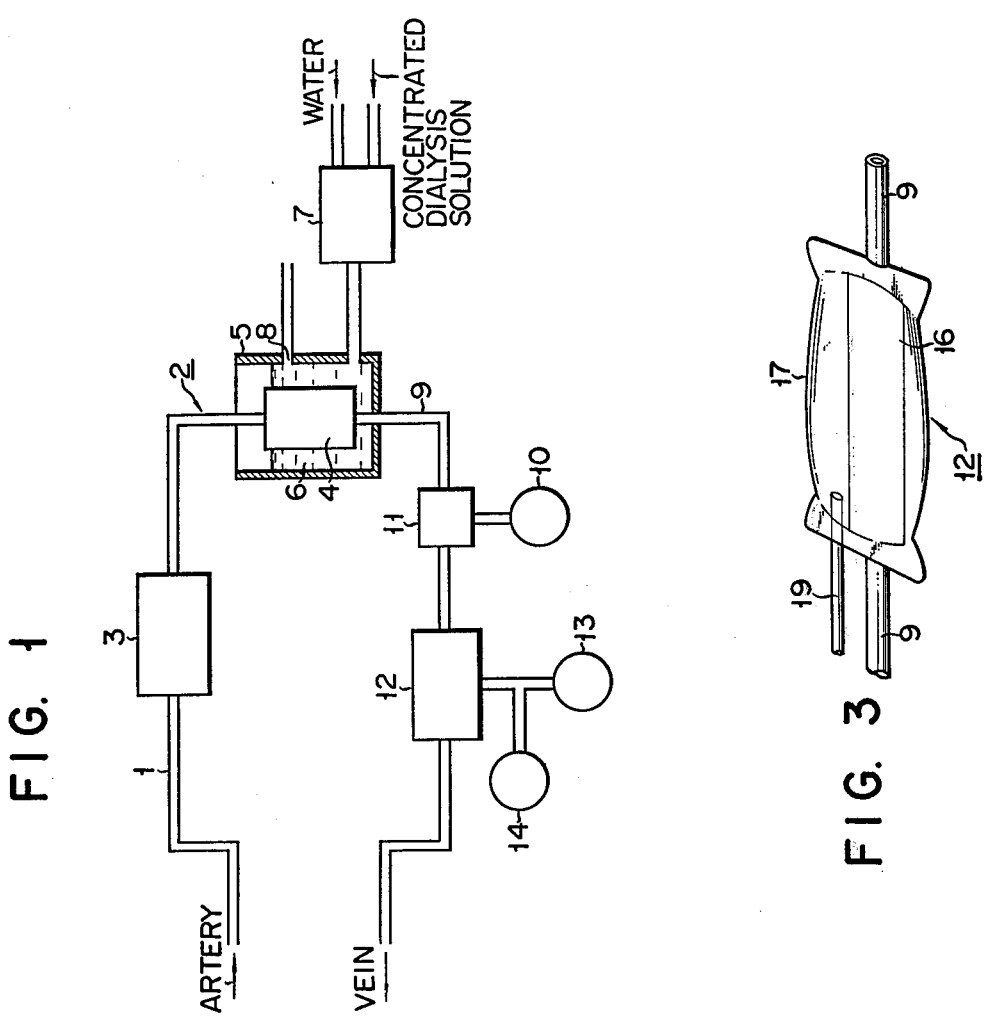
FIG. 1
FIG. 3

CLOSED CHAMBER

CLOSED CHAMBER

CLOSED CHAMBER

ARTIFICIAL KIDNEY DEVICE

This application is a continuation-in-part of my co-pending application Ser. No. 529,500 filed Dec. 4, 1975, now U.S. Pat. No. 3,986,956, issued Oct. 19, 1976.

BACKGROUND OF THE INVENTION

This invention relates to an artificial kidney device and in particular an artificial kidney device provided with a liquid pressure adjusting means for automatically maintaining an ultrafiltration pressure substantially constant and a safety means for preventing inflow of an excessive amount of gas to a human vein.

By "an ultrafiltration pressure" is meant a difference between internal and external pressures applied to a dialysis membrane consisting of a semipermeable membrane which is provided within a dialyzer.

A variety of artificial kidney devices, for example, a coil type, a keel type or a type utilizing hollow fibers has been known up to this date. These artificial kidney devices are adapted to send blood from the artery of human being through a suitable means to a dialyzer where urea, nitrogen, sodium, potassium, water content etc., included in blood are separated through a semipermeable membrane. The blood passed through the dialyzer is returned to the vein of the human being. With the dialyzer, the water content should be eliminated, in an amount far greater than that of the other components, through the semipermeable membrane. In addition to osmotic pressure, therefore, an additional pressure is generally required for the dialysis operation. One method is to apply ultrafiltration pressure to a dialyzer in an attempt to eliminate more water content. Taking the strength etc. of the semipermeable membrane into consideration, the ultrafiltration pressure is generally desired to be maintained at a level of 200 mm Hg. If the ultrafiltration pressure is too high, there is a fear that blood will flow out due to a breakage of the semipermeable membrane. If, on the other hand, it is too low, a dialyzing effect is lowered, and water content is not sufficiently eliminated from blood. For the purpose of maintaining the ultrafiltration pressure at suitable level, a method employed in a prior art positive pressure type artificial kidney device is to transport a pressurized blood from artery to a dialyzer by a pumping means and to mount a pinch-cock midway of a tube extending from a dialyzer into a vein of a human being. An ultrafiltration pressure can be provided by restricting the flow passage of the tube by means of the pinch-cock.

However, a very delicate operation of the pinch-cock is required in adjusting the ultrafiltration pressure. Any slight operation of the pinch-cock causes a greater change in the resistance of blood. To make the ultrafiltration pressure at a prescribed level, therefore, the adjustment of the pinch-cock is conducted gradually, i.e. by repeating the adjustment several times. It will take more than two minutes for ultrafiltration pressure to settle down to a prescribed level after one adjustment has been made. For this reason, more than ten minutes will be required in adjusting the ultrafiltration pressure to a desired level. If no due care should be exercised during adjustment, there is a chance that blood will flow out due to a breakage of the dialysis membrane.

The ultrafiltration pressure is related not only to the extent to which the pinch-cock is closed but also to the operation of means for transporting blood from the artery of a human being into a dialyzer, for example, rotations of a pump. If, therefore, the pump is changed in the number of rotations to increase a flow of blood, the above-mentioned delicate adjustment will be required on each occasion.

As a settlement to the above-mentioned problems, we proposed in U.S. patent application Ser. No. 529,500 an artificial kidney device equipped with pressure adjusting means for automatically maintaining at all times constant the ultrafiltration pressure of a dialyzer in spite of a change in an amount of blood, for example, a change of blood pressure or a change in the number of rotations of a pressure pump for blood.

FIG. 1 is a schematic diagram showing an artificial kidney device proposed in the above-mentioned U.S. Patent Application and also applicable to this invention which is provided with a coil type dialyzer. A tube 1 is connected at one end to the artery of a human being and at the other end to the dialyzer 2. Midway of the tube 1 is connected a pump 3 for sending blood to the dialyzer 2 at a predetermined flow rate. The dialyzer 2 is a known coil type formed by winding one or a plurality of semipermeable membranes, into a coil 4 with a mesh interposed therebetween and submerging the coil into a dialysis solution 6 within a container 5. The dialysis solution 6 from the mixer 7 is supplied to and discharged from an outlet 8 while it is contacted with a dialysis membrane.

On the other hand, blood is passed through the dialyzer 2, where unnecessary components are separated, and flows through a tube 9 into the vein of the human being. Midway of the tube 9, a drip tube 11 connected to a manometer 10 and a double-walled tube 12 connected to an air pump 13 and air reservoir 14 are provided in communication with the tube 9. FIG. 2 shows the details of the drip tube 11, the air pump 13, the air reservoir 14 and the double-walled tube 12. As shown in FIG. 2 the blood passed through the dialyzer 2 is sent through the tube 9 to the drip tube 11 and then flows through a mesh 15 into the double-walled tube 12. The double-walled tube 12 has an inner tube 16 as shown in FIGS. 3 to 6 and an outer tube 17. The inner tube 16 is made of a material which allows opening or closing of the tube 16 due to a slight difference in pressure occurring between the inside and outside of the inner tube 16. As shown in FIGS. 4 and 6, the inner tube 16 is formed by superposing one over the other two sheets of non-rigid polyvinyl chloride and sealing them at the side edge portions. The inner and outer tubes 16 and 17 of the double-walled tube 12 are hermetically heat sealed at each end to define a closed chamber 18 between the inner and outer tubes 16 and 17. The tube 19 is opened at one end into the closed chamber 18 and at the other end detachably connected to an air reservoir 20. A manually operated air pump 23 is connected through a tube 22 to the air reservoir 20 and adopted to adjust the air pressure prevailing within the air reservoir 20. 21 denotes a manometer for indicating an air pressure within the air reservoir 20. 24 and 25 denote valve means, respectively.

An explanation will now be made as to how an ultrafiltration pressure is automatically controlled in the so constructed artificial kidney device.

Blood from the artery of a human being is sent to the dialyzer 2. The air pump 23 is repeatedly squeezed for increasing pressure within the air reservoir 20 and closed chamber 18 so that a pressure prevailing within the dialysis coil of the dialyzer 2 comes to, for example, 200 mm Hg.

When the pressure within the dialysis coil 4 reaches 200 mm Hg, the valve 25 is closed and internal pressure in the inner tube 16 and closed chamber 18 takes an equilibrium state and the inner tube 16 is inflated to a suitable extent shown, for example, in FIGS. 4 and 6. When, however, the pressure within the dialysis coil 4 comes to below 200 mm Hg, the inner tube 16 of the double-walled tube 12 is collapsed as shown in FIGS. 5 and 7 with its opening being narrowed in cross section, since the internal pressure of the inner tube 16 is smaller than the external pressure of the inner tube 16. As the inner tube 16 is so collapsed, the blood passed through the dialysis coil is restricted, causing the ultrafiltration pressure to be recovered to a pressure of 200 mm Hg. In this way, the ultrafiltration pressure is automatically adjusted to 200 mm Hg. When, on the other hand, the pressure within the dialysis coil 4 exceeds 200 mm Hg, the internal pressure of the inner tube 16 exceeds the external pressure of the inner tube 16 causing the inner tube 16 to be again inflated as shown in FIGS. 4 and 6. As a result, blood flow rate is increased and the pressure prevailing within the dialysis coil is dropped and automatically adjusted to 200 mm Hg. In this way, the ultrafiltration pressure i.e. the pressure within the dialysis coil is automatically maintained to 200 mm Hg. This automatic adjustment is effected within several seconds to scores of seconds. In an automatic ultrafiltration pressure adjustment, the air reservoir 20 works as a pressure change absorbing means. A volume within the closed chamber 18 is somewhat changed due to the collapse or inflation of the inner tube 16. This change, however, is absorbed by a relatively great amount of air confined within the air reservoir 20. Consequently, the change of pressure within the closed chamber 18 due to the collapse or inflation of the inner tube 16 can be disregarded. From this viewpoint the greater the volume of the air reservoir 20, the better. The air reservoir 20 is, as above-explained, effective in an automatic adjustment of an ultrafiltration pressure. There is, however, a fear that if by any chance the inner tube 16 should be broken, a greater amount of air flows into the blood vessel of the human being. In this sense, the presence of the air reservoir 20 may also be considered as dangerous.

There are opinions in medical field that a volume of more than 20 cc of air entering into human vein would affect the health of human being in some way. Taking such a view into consideration it is advisable to prevent air from entering into human vein if by any chance.

SUMMARY OF THE INVENTION

It is accordingly the object of this invention to provide an artificial kidney device comprising a double-walled tube consisting of a flexible inner tube and nonflexible outer tube which is provided midway of a tube for a supply of blood from a dialyzer to a human vein, so as to permit ultrafiltration pressure to be automatically maintained to a predetermined value in which there is no malfunction in the adjustment of the ultrafiltration pressure and an entry of air into the vein can be restricted well within an allowable limit even in the event of a rupture of the double-walled tube.

According to the present invention, there is provided an artificial kidney device comprising a dialyzer for removing specified components from blood, a double-walled tube consisting of an inner tube mounted midway of a tube provided for transporting the blood passed through the dialyzer into a vein of a human being and communicating with the blood transporting tube, and an outer tube surrounding the inner tube to define a closed chamber therebetween, an air reservoir communicating through an outlet with the closed chamber for absorbing a pressure change within the closed chamber and pressure applying means for applying pressure to maintain an interior pressure within the closed chamber to a prescribed value, in which said inner tube is easily deformable and said outer tube is substantially undeformable under pressure to be applied by the pressure applying means, an ultrafiltration pressure is maintained substantially constant by a collapse or inflation of the inner tube effected by a difference in pressure between the inside and outside of the inner tube, and said air reservoir is provided with a movable partition means near the outlet of said air reservoir, thereby dividing the interior of the air reservoir into two.

BRIEF DESCRIPTION OF THE DRAWING

FIG. 1 is a schematic general view showing an artificial kidney device according to this invention;

FIG. 2 is a schematic view showing the major part of this invention;

FIG. 3 is an enlarged, perspective view showing a pressure adjusting means comprised of a double-walled tube;

DETAILED DESCRIPTION OF THE INVENTION

This invention is characterized in that, in an artificial kidney device as disclosed in the prior art U.S. patent application Ser. No. 529,500, an improved air reservoir is provided in communication with the closed chamber of the double-walled tube in an attempt to render as low as possible an air entry into a human vein even in the event of rupture of the inner wall of the double-walled tube, while at the same time well performing an ultrafiltration pressure adjustment function. The other arrangement and effects of the ultrafiltration adjustment mechanism as well as the operation of the device is the same as those shown in FIGS. 1 to 7 of the above-mentioned U.S. patent application.

Figure 4:
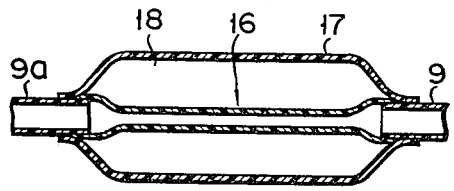
FIGS. 4 and 5 are longitudinal cross-sectional views respectively showing widely open and collapsed states of the pressure adjusting means of FIG. 3.
Figure 5:
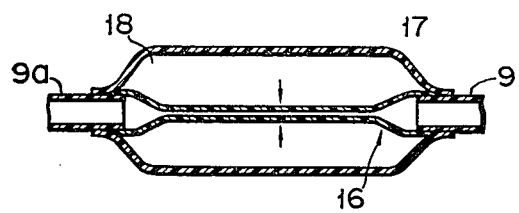
Figure 6:
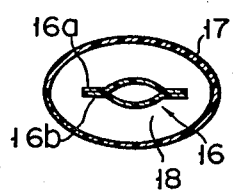
FIGS. 6 and 7 are cross-sectional views showing the pressure adjusting means of FIG. 3, each corresponding to FIG. 4 and FIG. 5.
Figure 7:
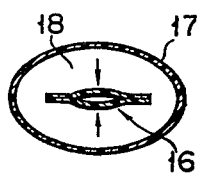
Figure 8:
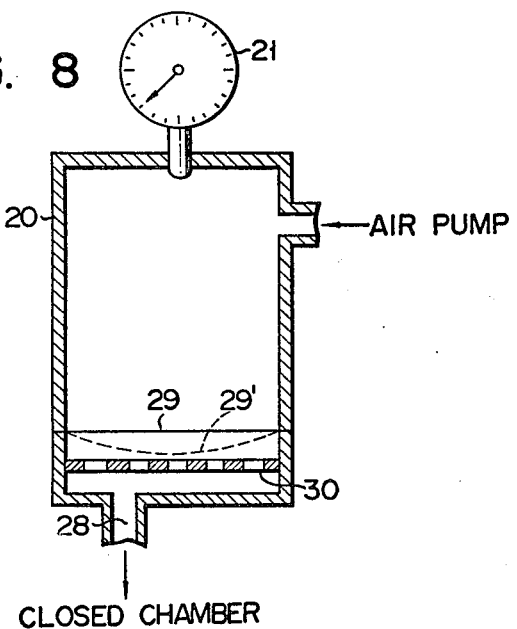
FIGS. 8, 9, 10 and 11 are cross-sectional views of various air reservoirs each equipped with a safety valve means in preparation against breakage of a double-walled tube.

FIGS. 8 to 11 show examples of partition means serving to prevent air from entering into blood, should the inner tube 16 be broken. In FIG. 8, an elastic film 29, acting as the partition means, made of rubber or the like is provided at the bottom side of the air reservoir 20 and adjacent to an outlet 28 leading to the closed chamber 18, so as to hermetically divide the air reservoir into two rooms. Slightly below the elastic film 29, a lattice 30 is provided as a stopper means for the elastic film 29 when the film 29 expands downward. A precise positioning of the stopper 30 may be determined taking into consideration downward inflations of the elastic film 29 due to an increased pressure inside the air reservoir 20 as well as due to the collapse of the inner tube 16.

If air is introduced into the air reservoir 20 by means of the air pump 23 in order to set the ultrafiltration pressure of the dialyzer at a predetermined value, the elastic film 29 expands downward as shown by a broken line 29′ in FIG. 8, thereby rendering equal pressure within the air reservoir 20, the closed chamber 18 and the inner tube 16. While the ultrafiltration pressure is kept at the predetermined value, the blood coming from the dialyzer is allowed to flow into the vein through the inner tube 16 kept open to an appropriate extent. If the ultrafiltration pressure is lowered below the predetermined value, the inner tube 16 contracts to control the blood flow as explained previously in conjunction with FIG. 5, thereby bringing automatically the ultrafiltration pressure back to the predetermined value.

The contraction of the inner tube 16 enlarges the space of the closed chamber 18 and, thus, the internal pressure of the chamber 18 may be decreased. But, a pressure drop does not take place in the device according to this invention, because the elastic film 29 expands downward (below the broken line 29′) in accordance with the contraction of the inner tube 16. Namely, the film 29 serves to absorb pressure fluctuation within the closed chamber 18. Likewise, if the ultrafiltration pressure exceeds the predetermined value, the inner tube 16 is opened wide to allow the passage of a large quantity of blood, thereby bringing the ultrafiltration pressure down to the predetermined value. In this case, the pressure fluctuation within the closed chamber 18 is absorbed as well by upward expansion (above the broken line 29′) of the elastic film 29.

As described above, the elastic film 29 hermetically separating the major part of the air reservoir 20 and the closed chamber 18 serves to absorb the pressure fluctuation within the closed chamber 18. Accordingly, the device of this invention performs the function equivalent to the case where the air reservoir 20 not equipped with an elastic film is directly connected to the closed chamber 18.

If the inner tube 16 should be broken, the air in the closed chamber 18, the tube 19 and the space below the elastic film 29 of the air reservoir 20 continues to enter into blood until the air pressure is lowered to the level of the blood pressure. In accordance with the decrease in the air pressure mentioned, the elastic film 29 expands downward, but the expansion is restricted by the lattice 30. Accordingly, most of the air within the air reservoir 20 is confined as it is and will not enter into blood.

As described above, the invented device for adjusting the ultrafiltration pressure permits providing an air reservoir large enough to absorb satisfactorily the air pressure fluctuation within the closed chamber 18. In addition, the entrance of air into blood can be minimized if the inner tube 16 should be broken. Namely, the safety of the device can be enhanced without impairing the function of adjusting the ultrafiltration pressure.

There will now be described some concrete examples. Now let it be assumed that the air reservoir 20 is chosen to have a volume of 70 cc, the total volume of the tube 19 and closed chamber 18 is set at 8 cc, and the tube and closed chambers 19, 18 are connected to the air reservoir 20 with no elastic film 20. If, in this case the inner tube 16 should be broken while the air reservoir 20 is kept at a pressure 300 mm Hg higher than the atmospheric, then as much as 30 cc of air will be carried into the blood to reduce air pressure in the air reservoir 20 to the atmospheric. On the other hand, if the air reservoir 20 is divided by an elastic film 29 into a room of 60 cc and another room of 10 cc, the volume of air in direct contact with the inner tube 16 is decreased to 18 cc (10 cc + 8 cc) in contrast to 78 cc (70 cc + 8 cc) for the above case. Accordingly, should the inner tube 16 be broken under the same conditions as above, the amount of air entering blood is decreased to 7 cc in contrast to 30 cc for the case where the elastic film 29 is not provided. If the incremental pressure of air is set at 200 mm Hg, the amounts of air entering blood are 20 cc and 4.7 cc where the elastic film 29 is not provided and is provided, respectively.

For reference, the elastic film 29 in a downwardly expanded state can be brought back to the original state as shown by a solid line in FIG. 8 if the pressures of the two rooms of the air reservoir 20 are made equal by releasing the valves 24, 25 of the air pump 23 and then by detaching the tube 19, thereby rendering the device ready for succeeding operations.

Figure 9:
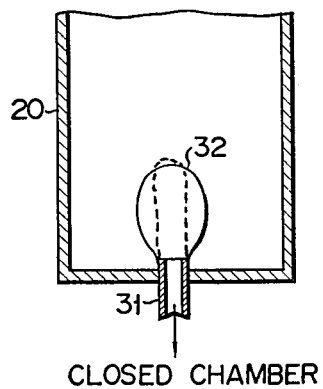

FIG. 9 is a cross sectional view of an air reservoir equipped with another example of partition means. Specifically, an elastic bulb 32 acting as partition means is hermetically fixed to a cylindrical outlet 31 projected inside the air reservoir 20. The outer end of the outlet is connected to the closed chamber 18. As is the case with a rubber bulb fixed to a syringe, the elastic bulb 32 is made of an elastic film such as rubber. Namely, if pressure is applied from outside, the interior volume of the elastic bulb 32 is caused to decrease and, upon removal of the pressure applied, the elastic bulb 32 is brought back to the normal state.

Apparently, the rubber bulb 32 is equivalent to the elastic rubber film 29 of FIG. 8 in terms of the function. The broken lines of FIG. 9 indicate a collapsed state of the elastic bulb 32. Needless to say, the pressure within the air reservoir 20 and the closed chamber 18 are kept equal by deformation of the elastic bulb 32. Attentions should be paid to an additional advantage of the elastic bulb 32 over the rubber film 29 of FIG. 8. Namely, should the inner tube of the double-walled tube be broken, the rubber bulb 32 is completely collapsed to minimize the amount of air entering into blood. Thus, the device of FIG. 9 does not necessitate a stopper like a lattice 30 of FIG. 8, enabling the construction to be simplified to a large extent.

Figure 10:
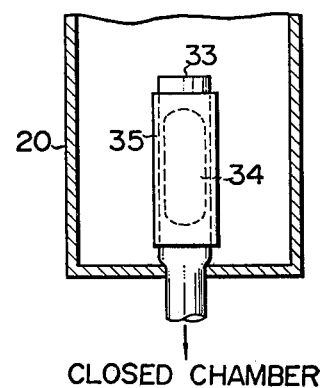

FIG. 10 illustrates still another embodiment of a partition means, in which is provided a pipe 33 projected into the interior of the air reservoir 20 and leading to the tube 19. The uppermost edge of the pipe 33 is closed and a window 34 is provided on a side of the pipe 33. In this case, the window 34 is covered with a rubber tube 35. Apparently, the pressure fluctuation within the closed chamber 18 can be fully absorbed by the elastic deformation of the rubber tube 35. In addition, the amount of air entering into the blood can be minimized if the inner tube 16 should be broken by accident.

Figure 11:
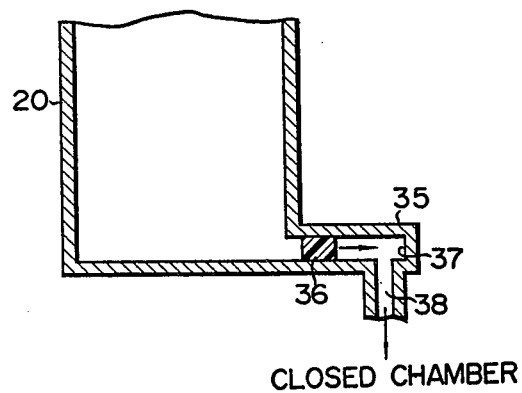

FIG. 11 illustrates still another embodiment of partition means, in which is provided at a bottom portion of the air reservoir 20 an outlet tube 35 having an outlet 38 leading to the tube 19. In this case, a movable piston 36 acting as a partition means is slidably and hermetically inserted into the outlet tube 35. Accordingly, the pressure fluctuation within the closed chamber 18 can be absorbed by the corresponding movement of the piston 36, thereby performing the adjustment function of the ultrafiltration pressure within the dialyzer. In addition, should the inner tube 16 be broken, the movable piston 36 is allowed to contact a wall 37 of the outlet tube 35, thereby closing the outlet 38 communicating the closed chamber 18 with the air reservoir 20. This minimizes the amount of air entering into blood in the event of breakage of the inner tube 16. Apparently, the device of FIG. 11 is equivalent in function to the device of FIG. 8.

The artificial kidney device according to this invention may be applied not only to the above-mentioned coil type dialyzer, but also to all dialyzers, including one using hollow fibers, which are adapted to effect dialysis utilizing an ultrafiltration pressure.

The above-described embodiment is for a case where invented devices for adjusting the ultrafiltration pressure are applied to an artificial kidney device. But, the application of this invention is not limited thereto. This invention can be applied to automatic pressure adjustments of other fluids as well.

Though with the above-mentioned embodiment the air pressure is applied to the closed chamber, any fluid pressure may be applied to the closed chamber. Use of water, however, assures a safety against the possible breakage of the inner tube 16.

The "air reservoir" as herein defined in this specification should not be restricted to a type which receives an air only. It should be noted that it also includes a type which can receive any other gas.

What is claimed is:

1. An artificial kidney device for a human being comprising:
    a dialyzer for removing specified components from blood;
    blood pumping means for transporting blood from an artery of the human being to the dialyzer and creating a blood pressure in the dialyzer above arterial pressure;
    means forming a flow passage in communication with said dialyzer for transporting blood passed through the dialyzer to a vein of the human being;
    means for maintaining a substantially constant ultrafiltration pressure in said dialyzer including an inner tube forming part of said flow passage and an outer tube surrounding said inner tube and defining a closed chamber therewith, the pressure within said inner tube being subject to change in accordance with prevailing blood pressure in said dialyzer;
    means for providing a substantially constant predetermined pressure in excess of atmospheric pressure within said closed chamber;
    said inner tube being formed of material deformable in response to pressure differentials created between the inside of said inner tube and said chamber to enlarge or restrict said flow passage through said inner tube so that the pressure inside said inner tube will balance the substantially constant predetermined pressure in said closed chamber to thereby maintain said ultrafiltration pressure in the dialyzer substantially constant;
    means including a gas filled reservoir coupled with said chamber for absorbing any pressure fluctuation in said chamber in response to deformation of said inner tube, and
    means for preventing ingress of gas from said reservoir into said chamber thereby minimizing the quantity of gas flowing into said flow passage in the event of a rupture of said inner tube.

2. The device according to claim 1 including movable partition means in said reservoir dividing its interior into two compartments, one of said compartments having an outlet in communication with said chamber.

3. The device according to claim 2 wherein said partition means comprises an elastic film for hermetically sealing the compartments one from the other, said film being deformable in accordance with a pressure differential on opposite sides thereof, and means for constraining said elastic film for deformation in a predetermined range.

4. The device according to claim 3 wherein said constraining means comprises a latticed board disposed adjacent said elastic film and between said elastic film and said outlet.

5. The device according to claim 2 wherein said partition means includes an elastic bulb hermetically sealed about said outlet and adapted to obtain a predetermined volume upon equalization of the pressure across said bulb.

6. The device according to claim 5 wherein said outlet includes a pipe having one end extending into said reservoir, said elastic bulb being comprised of a rubber bulb hermetically connected to said one pipe end.

7. The device according to claim 2 wherein said partition means includes an elastic bulb hermetically sealed about said outlet and having a predetermined volume upon equalization of the pressure across said bulb, said elastic bulb being collapsible in the event of a rupture of said inner tube to close the opening of said outlet.

8. The device according to claim 2 including a pipe in communication with said outlet and having an opening through a side surface thereof, said partition means including an elastic tube covering said opening.

9. The device according to claim 1 wherein said reservoir includes an outlet coupled to said chamber, said partition means including a movable piston substantially sealing said outlet and slidable in said outlet in accordance with a pressure differential on opposite sides of said piston.

10. An artificial kidney device according to claim 2 wherein the volume of said one compartment, when said ultrafiltration pressure in the dialyzer is maintained substantially constant, is small in comparison with the volume of the other compartment in said reservoir.

11. An artificial kidney device for a human being comprising:
    a dialyzer for removing specified components from blood;
    means for transporting blood from a bloodvessel of the human being to the dialyzer and creating a blood pressure in the dialyzer above arterial pressure;
    means forming a flow passage in communication with said dialyzer for transporting blood passed through the dialyzer to a bloodvessel of the human being;
    means for maintaining a substantially constant ultrafiltration pressure in said dialyzer including means defining a passageway forming part of said flow passage, means defining a closed chamber and a deformable material disposed between and forming a part of said passageway and said chamber, the pressure within said passageway being subject to change in accordance with prevailing blood pressure in said dialyzer;

means for providing a substantially constant predetermined pressure in excess of atmospheric pressure within said closed chamber;

said deformable material being responsive to pressure differentials created between said passageway and said chamber to enlarge or restrict said flow passage through said passageway so that the pressure within said passageway will balance the substantially constant predetermined pressure in said closed chamber to thereby maintain said ultrafiltration pressure in the dialyzer substantially constant;

means including a gas filled reservoir coupled with said chamber for absorbing pressure fluctuation in said chamber in response to deformation of said deformable material; and means for preventing ingress of gas from said reservoir into said chamber thereby minimizing the quantity of gas flowing into said flow passage in the event of a rupture of said deformable material.

12. The device according to claim 11 including movable partition means in said reservoir dividing its interior into two compartments, one of said compartments having an outlet in communication with said chamber.

13. The device according to claim 12 wherein said partition means comprises an elastic film for hermetically sealing the compartments one from the other, said film being deformable in accordance with a pressure differential on opposite sides thereof, and means for constraining said elastic film for deformation in a predetermined range.

14. The device according to claim 13 wherein said constraining means comprises a latticed board disposed adjacent said elastic film and between said elastic film and said outlet.

15. The device according to claim 12 wherein said partition means includes an elastic bulb hermetically sealed about said outlet and adapted to obtain a predetermined volume upon equalization of the pressure across said bulb.

16. The device according to claim 15 wherein said outlet includes a pipe having one end extending into said reservoir, said elastic bulb being comprised of a rubber bulb hermetically sealed about said one pipe end.

17. The device according to claim 12 including a pipe in communication with said outlet and having an opening through a side surface thereof, said partition means including an elastic tube covering said opening.

18. An artificial kidney device according to claim 12 wherein the volume of said one compartment, when said ultrafiltration pressure in the dialyzer is maintained substantially constant, is small in comparison with the volume of the other compartment in said reservoir.

19. The device according to claim 11 wherein said partition means includes an elastic bulb hermetically sealed about said outlet and having a predetermined volume upon equalization of the pressure across said bulb, said elastic bulb being collapsible in the event of a rupture of said deformable material to close the opening of said outlet.

20. The device according to claim 11 wherein said reservoir includes an outlet coupled to said chamber, said partition means including a movable piston substantially sealing said outlet and slidable in said outlet in accordance with a pressure differential on opposite sides of said block.

21. An artificial kidney device for a human being comprising:

a dialyzer for removing specified components from blood;

blood pumping means for transporting blood from an artery of the human being to the dialyzer and creating a blood pressure in the dialyzer above arterial pressure;

means forming a flow passage in communication with said dialyzer for transporting blood passed through the dialyzer to a vein of the human being;

means for maintaining a substantially constant ultrafiltration pressure in said dialyzer including means defining a passageway forming part of said flow passage, means defining a closed chamber, and a deformable material disposed between and forming a part of said passageway and said chamber, the pressure within said passageway being subject to change in accordance with prevailing blood pressure in said dialyzer; and means for providing a substantially constant predetermined pressure in excess of atmospheric pressure within said closed chamber including a gas filled reservoir coupled with said chamber, movable partition means in said reservoir dividing it into two compartments with one of said compartments in communication with said chamber, and means for supplying gas under pressure to the other of said compartments to move said partition means to a location at which the pressure on opposite sides of said partition means is substantially equalized thereby obtaining said predetermined pressure within said closed chamber, said deformable material being responsive to pressure differentials created between said passageway and said chamber to enlarge or restrict said flow passage through said passageway so that the pressure within said passageway will balance the substantially constant predetermined pressure in said closed chamber to thereby maintain said ultrafiltration pressure in the dialyzer substantially constant;

said partition means preventing ingress of gas from said other compartment into said chamber thereby minimizing the quantity of gas flowing into said flow passage in the event of a rupture of said deformable material.

22. The device according to claim 21 wherein said one compartment communicates with said chamber through an outlet, said partition means including an elastic bulb hermetically sealed about said outlet and adapted to obtain a predetermined volume upon equalization of the pressure across said bulb.

23. The device according to claim 22 wherein said outlet includes a pipe having one end extending into said one compartment, said elastic bulb being comprised of a rubber bulb hermetically connected to said one pipe end.

24. The device according to claim 21 wherein said partition means includes an elastic bulb hermetically sealed about said outlet and having a predetermined volume upon equalization of the pressure across said bulb, said elastic bulb being collapsible in the event of a rupture of said deformable material to close the opening of said outlet.

25. The device according to claim 21 wherein said partition means includes an elastic bulb hermetically sealed about said outlet and having a predetermined volume upon equalization of the pressure across said bulb, said elastic bulb being collapsible in the event of a rupture of said deformable material to close the opening of said outlet; said gas supplying means including a hand air-pump; and said gas filled reservoir including a pressure measuring means connected to said other compartment for indicating a gas pressure within the reservoir.

26. The device according to claim 21 wherein said one compartment communicates with said chamber through an outlet, a pipe in communication with said outlet and having an opening through a side surface thereof, said partition means including an elastic tube covering said opening.

27. The device according to claim 21 wherein said partition means serves to absorb any pressure fluctuation in said chamber in response to deformation of said deformable material.

28. An artificial kidney device according to claim 21 wherein the volume of said one compartment, when said ultrafiltration pressure in the dialyzer is maintained substantially constant, is small in comparison with the volume of the other compartment in said reservoir.

29. An artificial kidney device for a human being comprising:
  a dialyzer for removing specified components from blood;
  blood pumping means for transporting blood from an artery of the human being to the dialyzer and creating a blood pressure in the dialyzer above arterial pressure;
  means forming a flow passage in communication with said dialyzer for transporting blood passed through the dialyzer to a vein of the human being;
  means for maintaining a substantially constant ultrafiltration pressure in said dialyzer including an inner tube forming part of said flow passage and an outer tube surrounding said inner tube and defining a closed chamber therewith, the pressure within said inner tube being subject to change in accordance with prevailing blood pressure in said dialyzer;
  means for providing a substantially constant predetermined pressure in excess of atmospheric pressure within said closed chamber including a gas filled reservoir coupled with said chamber, movable partition means in said reservoir dividing it into two compartments with one of said compartments in communication with said chamber, and means for supplying gas under pressure to the other of said compartment to move said partition means to a location at which the pressure on opposite sides of said partition means is substantially equalized thereby obtaining said predetermined pressure within said closed chamber;
  said inner tube being formed of material deformable in response to pressure differentials created between the inside of said inner tube and said chamber to enlarge or restrict said flow passage through said inner tube so that the pressure inside said inner tube will balance the substantially constant predetermined pressure in said closed chamber to thereby maintain said ultrafiltration pressure in the dialyzer substantially constant;
  said reservoir serving to absorb any pressure fluctuation in said chamber in response to deformation of said inner tube,
  said partition means preventing ingress of gas from said other compartment into said chamber thereby minimizing the quantity of gas flowing into said flow passage in the event of a rupture of said inner tube.

30. The device according to claim 29 wherein said one compartment communicates with said chamber through an outlet, said partition means including an elastic bulb hermetically sealed about said outlet and adapted to obtain a predetermined volume upon equalization of the pressure across said bulb.

31. The device according to claim 30 wherein said outlet includes a pipe having one end extending into said one compartment, said elastic bulb being comprised of a rubber bulb hermetically connected to said one pipe end.

32. The device according to claim 29 wherein said partition means includes an elastic bulb hermetically sealed about said outlet and having a predetermined volume upon equalization of the pressure across said bulb, said elastic bulb being collapsible in the event of a rupture of said inner tube to close the opening of said outlet.

33. The device according to claim 29 wherein said one compartment communicates with said chamber through an outlet, a pipe in communication with said outlet and having an opening through a side surface thereof, said partition means including an elastic tube covering said opening.

34. An artificial kidney device according to claim 29 wherein the volume of said one compartment, when said ultrafiltration pressure in the dialyzer is maintained substantially constant, is small in comparison with the volume of the other compartment in said reservoir.

* * * * *